United States Patent
Dhere et al.

(10) Patent No.: US 10,729,780 B2
(45) Date of Patent: Aug. 4, 2020

(54) METHODS FOR IMPROVING THE ADSORPTION OF POLYSACCHARIDE-PROTEIN CONJUGATES AND MULTIVALENT VACCINE FORMULATION OBTAINED THEREOF

(71) Applicant: Serum Institute of India Private Ltd., Hadapsar, Pune, Maharashta (IN)

(72) Inventors: Rajeev Mhalasakant Dhere, Maharashta (IN); Hitesh Kumar Malviya, Maharashta (IN); Swapan Kumar Jana, Maharashta (IN); Sambhaji Shankar Pisal, Maharashta (IN); Asha Dinesh Mallya, Maharashta (IN); Sunil Mahor, Maharashta (IN); Manish Maheshkumar Gautam, Maharashta (IN); Chetan Vilas Joshi, Maharashta (IN); Venkata Vamsi Krishna Malepati, Maharashta (IN); Prashant Shivaji Jadhav, Maharashta (IN)

(73) Assignee: Serum Institute of India Private Ltd., Hadapsar (IN)

( * ) Notice: Subject to any disclaimer, the term of this patent is extended or adjusted under 35 U.S.C. 154(b) by 0 days.

(21) Appl. No.: 15/580,653

(22) PCT Filed: Jun. 3, 2016

(86) PCT No.: PCT/IB2016/053265
§ 371 (c)(1),
(2) Date: Dec. 7, 2017

(87) PCT Pub. No.: WO2016/199003
PCT Pub. Date: Dec. 15, 2016

(65) Prior Publication Data
US 2018/0161445 A1 Jun. 14, 2018

(30) Foreign Application Priority Data
Jun. 8, 2015 (IN) .................. 2185/MUM/2015

(51) Int. Cl.
| | | |
|---|---|---|
| A61K 47/64 | (2017.01) | |
| A61K 39/00 | (2006.01) | |
| A61K 39/085 | (2006.01) | |
| A61K 39/09 | (2006.01) | |
| A61K 39/116 | (2006.01) | |
| A61K 39/39 | (2006.01) | |
| A61K 47/02 | (2006.01) | |
| A61K 47/12 | (2006.01) | |
| A61K 47/22 | (2006.01) | |

(52) U.S. Cl.
CPC ............ *A61K 47/646* (2017.08); *A61K 39/00* (2013.01); *A61K 39/085* (2013.01); *A61K 39/09* (2013.01); *A61K 39/092* (2013.01); *A61K 39/116* (2013.01); *A61K 39/39* (2013.01); *A61K 47/02* (2013.01); *A61K 47/12* (2013.01); *A61K 47/22* (2013.01); *A61K 47/6415* (2017.08); *A61K 2039/545* (2013.01); *A61K 2039/55516* (2013.01); *A61K 2039/6037* (2013.01)

(58) Field of Classification Search
None
See application file for complete search history.

(56) References Cited

U.S. PATENT DOCUMENTS

| | | |
|---|---|---|
| 5,623,057 A | 4/1997 | Marburg et al. |
| 2007/0110762 A1 | 5/2007 | Jessouroun et al. |
| 2010/0209450 A1 | 8/2010 | Biemans et al. |
| 2011/0195086 A1 | 8/2011 | Caulfield et al. |
| 2014/0377302 A1 | 12/2014 | Kapre et al. |

FOREIGN PATENT DOCUMENTS

EP 2865392 A1 4/2015

OTHER PUBLICATIONS

Nurkka et al. Vaccine (20) 2002 194-201.*

* cited by examiner

*Primary Examiner* — Oluwatosin A Ogunbiyi
(74) *Attorney, Agent, or Firm* — Edwin A. Sisson, Attorney at Law, LLC; Jeffrey J. Banyas

(57) ABSTRACT

The present invention provides methods for preparation of stable multivalent pneumococcal polysaccharide-protein conjugate vaccine formulations. Instant stable formulations show optimal percent adsorption for each conjugate wherein, aggregation can be prevented by employing i) Individual or separate adsorption for conjugates that otherwise show lower percent adsorption by combined adsorption ii) Histidine-Succinic acid buffer system along with shift in pH from neutral pH to acidic pH iii) a polysaccharide to protein ratio between 0.5 to about 1.4 iv) a six-bladed Rushton type turbine impeller in formulation vessels.

8 Claims, 13 Drawing Sheets

Figure 1:
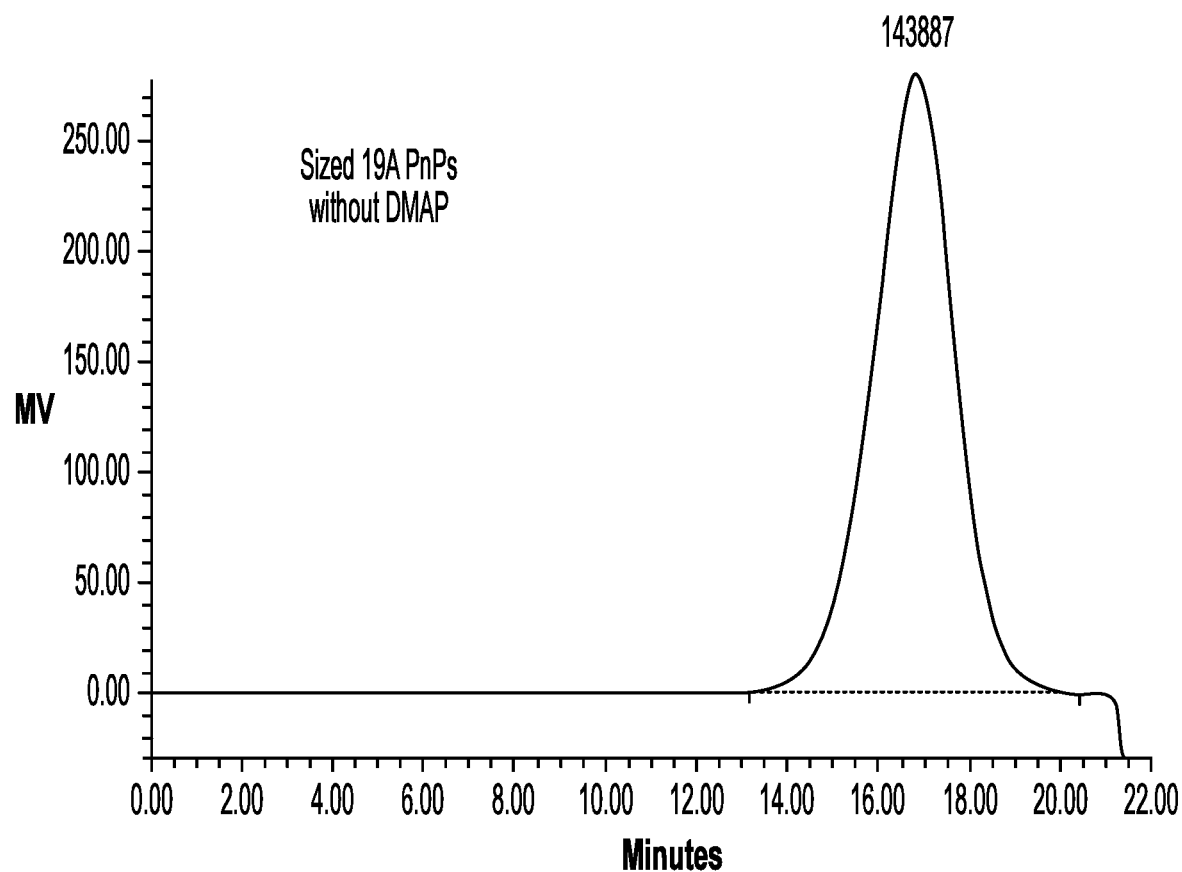

| | Peak Name | RT | Area | Mw (Da) | Mn (Da) | MP (Da) | % Area | Polydispersity |
|---|---|---|---|---|---|---|---|---|
| 1 | Peak 4 | 16,881 | 36050010 | 178357 | 124375 | 143887 | 100.00 | 1.434025 |

| | Peak Name | RT | Area | Mw (Da) | Mn (Da) | MP (Da) | % Area | Polydispersity |
|---|---|---|---|---|---|---|---|---|
| 1 | Peak 8 | 18,120 | 16821344 | 69941 | 37105 | 61650 | 100.00 | 1.884959 |

| | Peak Name | RT | Area | Mw (Da) | Mn (Da) | MP (Da) | % Area | Polydispersity |
|---|---|---|---|---|---|---|---|---|
| 1 | Broad | 16,417 | 561317 | 224030 | 194108 | 191587 | 1.62 | 1.154181 |
| 2 | Peak 9 | 19,875 | 34140780 | 14487 | 9007 | 11712 | 98.38 | 1.606378 |

| | Peak Name | RT | Area | Mw (Da) | Mn (Da) | MP (Da) | % Area | Polydispersity |
|---|---|---|---|---|---|---|---|---|
| 1 | Peak 4 | 16,881 | 36050010 | 178357 | 124375 | 143887 | 100.00 | 1.434025 |

| | Peak Name | RT | Area | Mw (Da) | Mn (Da) | MP (Da) | % Area | Polydispersity |
|---|---|---|---|---|---|---|---|---|
| 1 | Peak 4 | 17,144 | 16882446 | 254221 | 114791 | 121766 | 100.00 | 2.214838 |

| | Peak Name | RT | Area | Mw (Da) | Mn (Da) | MP (Da) | % Area | Polydispersity |
|---|---|---|---|---|---|---|---|---|
| 1 | Broad | 14,123 | 9442789 | 487267 | 172206 | 941445 | 100.00 | 2.829559 |

| | Peak Name | RT | Area | Mw (Da) | Mn (Da) | MP (Da) | % Area | Polydispersity |
|---|---|---|---|---|---|---|---|---|
| 1 | Broad | 13,860 | 10289208 | 1173521 | 911209 | 1150119 | 44.70 | 1.287873 |
| 2 | Peak 4 | 17,373 | 12731305 | 173846 | 114964 | 117250 | 55.30 | 1.612173 |

| | Peak Name | RT | Area | Mw (Da) | Mn (Da) | MP (Da) | % Area | Polydispersity |
|---|---|---|---|---|---|---|---|---|
| 1 | Broad | 13,243 | 16128396 | 898464 | 499923 | 1008801 | 100.00 | 1.797203 |

| | Peak Name | RT | Area | Mw (Da) | Mn (Da) | MP (Da) | % Area |
|---|---|---|---|---|---|---|---|
| 1 | Broad | 13,729 | 15487260 | 1098757 | 619271 | 1189617 | 100.00 |

| | Peak Name | RT | Area | Mw (Da) | Mn (Da) | MP (Da) | % Area | Polydispersity |
|---|---|---|---|---|---|---|---|---|
| 1 | Peak 4 | 16,980 | 12939746 | 166907 | 113770 | 133136 | 100.00 | 1.467050 |

| | Peak Name | RT | Area | Mw (Da) | Mn (Da) | MP (Da) | % Area | Polydispersity |
|---|---|---|---|---|---|---|---|---|
| 1 | Peak 4 | 17,192 | 8884468 | 156239 | 99497 | 115983 | 100.00 | 1.570293 |

| | Peak Name | RT | Area | Mw (Da) | Mn (Da) | MP (Da) | % Area | Polydispersity |
|---|---|---|---|---|---|---|---|---|
| 1 | Peak 4 | 16,940 | 5091525 | 161255 | 116007 | 141922 | 100.00 | 1.390010 |

| | Peak Name | RT | Area | Mw (Da) | Mn (Da) | MP (Da) | % Area | Polydispersity |
|---|---|---|---|---|---|---|---|---|
| 1 | Peak 4 | 16,952 | 9921138 | 161360 | 114430 | 140847 | 100.00 | 1.410112 |

METHODS FOR IMPROVING THE ADSORPTION OF POLYSACCHARIDE-PROTEIN CONJUGATES AND MULTIVALENT VACCINE FORMULATION OBTAINED THEREOF

PRIORITIES AND CROSS REFERENCES

This Application claims priority from International Application No. PCT/IB2016/053265 filed on 3 Jun. 2016 and Indian Patent Application No. 2185/MUM/2015 filed on 8 Jun. 2015, the teaching of each of which are hereby incorporated by reference in their entirety.

BACKGROUND OF THE INVENTION

*Streptococcus pneumoniae* is a leading cause of bacterial pneumonia, meningitis, and sepsis in children. Recent estimates of child deaths caused by *S. pneumoniae* range from 0.7-1.0 million every year worldwide. In 2000, about 14.5 million episodes of serious pneumococcal disease (uncertainty range 11.1-18.0 million) were estimated to occur. Pneumococcal disease caused about 0.826 million deaths (0.58-0.926 M) in children aged 1-59 months, of which 0.091 million (0.063-0.1 M) were in HIV-positive and 0.735 million (0.51-0.82 M) in HIV-negative children.

The multivalent pneumococcal polysaccharide vaccines that have been licensed for many years have proved valuable in preventing pneumococcal disease in adults, particularly, the elderly and those at high-risk. However, infants and young children respond poorly to unconjugated pneumococcal polysaccharides. The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000.

Further Prevnar™ 13 (Wyeth) is an approved vaccine that contains conjugates of polysaccharides from serotypes 6A, 6B, 19A, 19F in addition to 1, 3, 4, 5, 7F, 9V, 14, 18C and 23F. Synflorix™ (GSK) is another approved vaccine that provides protection against 1, 4, 5, 6B, 7F, 9V, 14, 18C, 19F, and 23F as well as cross protection against 19A & 6A.

Vaccine formulations must generally be stable and be of uniform consistency to accommodate the need for a long shelf-life and the use of multiple dose containers. Vaccines based on proteins, including polysaccharide-protein conjugates, are subject to protein aggregation and precipitation which can result in an effective lower total concentration of the vaccine due to the unavailability of the precipitated protein product. Polysaccharide-protein conjugate vaccines, in particular, appear to have a stronger tendency to aggregate than the carrier protein alone (See Berti et al, 2004, Biophys J 86:3-9). The choice of formulation for a polysaccharide-protein conjugate vaccine can greatly affect protein aggregation. See Ho et al., 2001, Vaccine 19:716-725.

Inspite of several existing multivalent pneumococcal polysaccharide-protein conjugate vaccine compositions being developed worldwide, there is an ongoing need in the art for vaccine formulations that provide high adsorption of individual conjugates and free from the aggregation/precipitation of immunogenic compositions having polysaccharide-protein conjugates.

The adjuvants traditionally used in such multivalent pneumococcal vaccines have been aluminium salts such as aluminium hydroxide and aluminium phosphate. Many other experimental adjuvants are known, however adsorption to aluminium salts remains the most common vaccine adjuvant formulation. Although their use is widespread, aluminium salts may not always be compatible with particular antigens thereby resulting in significant variations with respect to percent adsorption of polysaccharide-protein conjugate on alum or the antigenicity.

Immunological properties and stability of conjugate vaccine candidate adsorbed on aluminium adjuvants depends on various parameters like i) antigenicity of each antigen, ii) type of carrier protein used for conjugation, and iii) the type of adjuvant used. Most importantly, the extent of adsorption of antigen on the adjuvant has been previously reported to be one of the key parameters to demonstrate the lot to lot consistency of the formulation process and its possible impact on the efficacy of the vaccine product. Further, percent adsorption of polysaccharide-protein conjugates may drop further on storage of the formulation or under the adverse situations like temperature excursions. Refer 54th meeting of the WHO Expert Committee on Biological Standardization, Recommendations for the production & control of Pneumococcal conjugate vaccines, 17-21 Nov. 2003; Carl E. Frasch, Session IV: Conjugate Vaccines; Vaccine Technology II; Portugal. 2008.

As per European regulatory agency (EMEA) guidelines for pneumococcal polysaccharide-protein conjugates, completeness of adsorption (% unbound conjugate) should be considered as a crucial quality control parameter along with alum content, sterility, identity and free polysaccharide content. Refer Assessment Report for Synflorix 2009, Procedure No. EMEA/H/C/000973. WHO recommends maximizing adsorption for alum-precipitated antigens (e.g. diphtheria and tetanus toxoid) wherein at least 80% of the antigens in these vaccines be adsorbed.

During manufacturing of polysaccharide-protein conjugate, formulate can comprise of aggregates of polysaccharide-polysaccharide type, protein-protein type or polysaccharide-protein type. Such aggregations are also observed in the finished product leading to rejection of 4% to 10% of filled vials of polysaccharide-protein conjugate(s) vaccine, thereby affecting the stability and efficacy of the conjugate vaccine.

Given the above discussed limitations with respect to the aggregation and stability of the polysaccharide and its conjugate, there remains a distinct need for reducing aggregation and stabilizing said polysaccharide across downstream processing to the final formulation stage of Pneumococcal Conjugate Vaccine Manufacturing.

SUMMARY OF THE INVENTION

The invention provides improvements in the stability of vaccines which include aluminium salts, and in particular methods for minimizing aggregation and improvements in percent adsorption of individual conjugates in a multivalent pneumococcal polysaccharide-protein conjugate vaccines. The inventors of present invention have observed that combined adsorption of polysaccharide-protein conjugates and use of polysaccharide to protein ratio greater than 1:1 results in i) percent adsorption of less than 55% for *S. pneumoniae* conjugates for serotypes 6A, 9V and 23F and ii) percent adsorption from about 80% to 90% for remaining serotype conjugates, thereby failing to achieve complete adsorption for an individual serotype conjugate for a given multivalent pneumococcal conjugate formulation. Also it was observed that vaccine formulation prepared by using pH between 6.8 to 7.0 resulted in an aggregation of about 4 to 10% and lower adsorption.

The instant invention relates to a method for the preparation of a stable multivalent pneumococcal polysaccharide-protein conjugate vaccine formulation, showing optimal adsorption between 75 to 99% for each conjugate wherein, in said method, aggregation is prevented by employing at least one of:
  a. Individual or separate adsorption for conjugates that otherwise show relative lower adsorption by combined adsorption;
  b. Histidine-Succinic acid buffer system along with shift in pH from neutral pH to acidic pH;
  c. A polysaccharide to protein ratio between 0.6 to about 1.4; and/or
  d. The use of a six bladed Rushton type turbine impeller in the formulation vessel.

The instant invention also discloses a method for preparing polysaccharide-protein conjugates with improved immunogenicity and less free polysaccharide content for *Streptococcus pneumoniae* polysaccharides containing phosphodiester linkage, particularly 19A, 19F, 6A and 6B. Said conjugation process minimizes cyanylation agent byproduct mediated degradation of sized polysaccharide and prevents subsequent polysaccharide-polysaccharide aggregation thereby stabilizing labile polysaccharides. A key to reduced aggregation can be attributed to the use of a sized polysaccharide in the range of 100-200 KDa, and polysaccharide to CDAP (Cyanylation agent) ratio in the range of (1):(0.8-1).

The immunogenic composition prepared as per the instant invention provides reduced aggregation between Polysaccharide-Polysaccharide, and Polysaccharide-Protein Conjugate along with improved stability and immunogenicity.

FIGURES

Figure 2A:
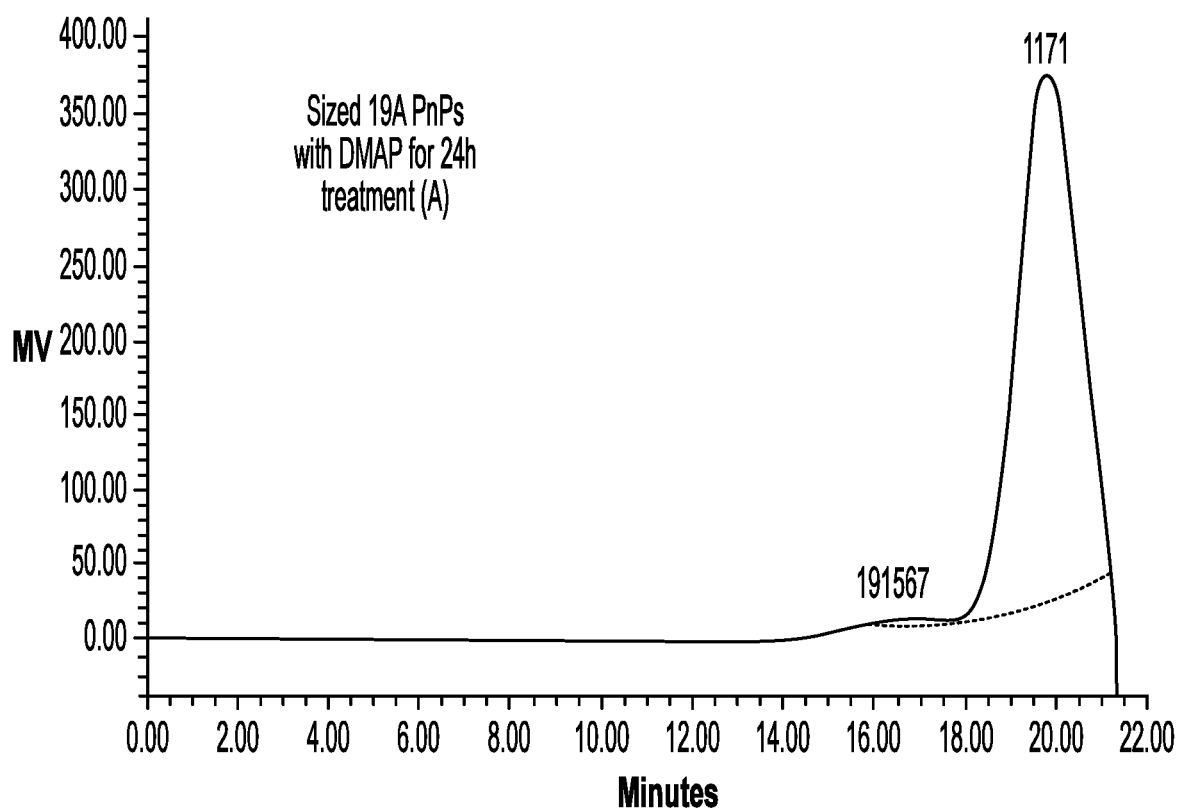
Figure 2B:
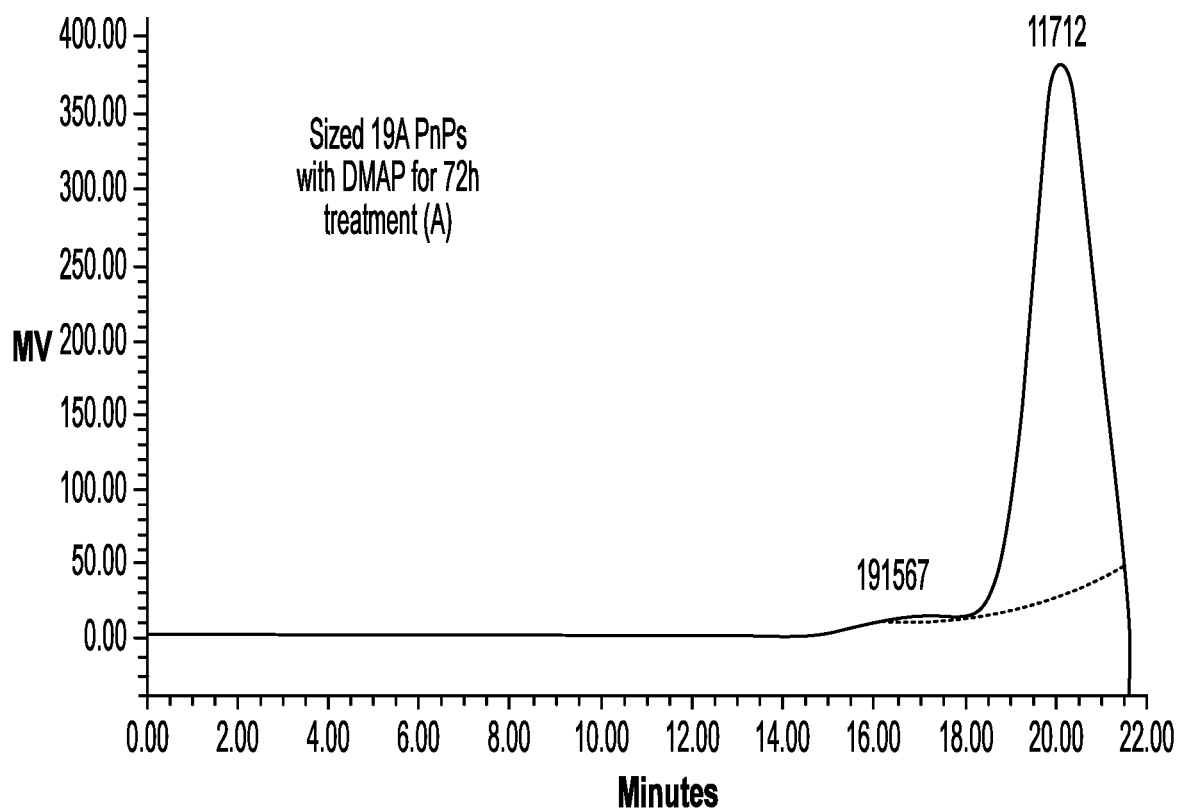
Figure 3A:
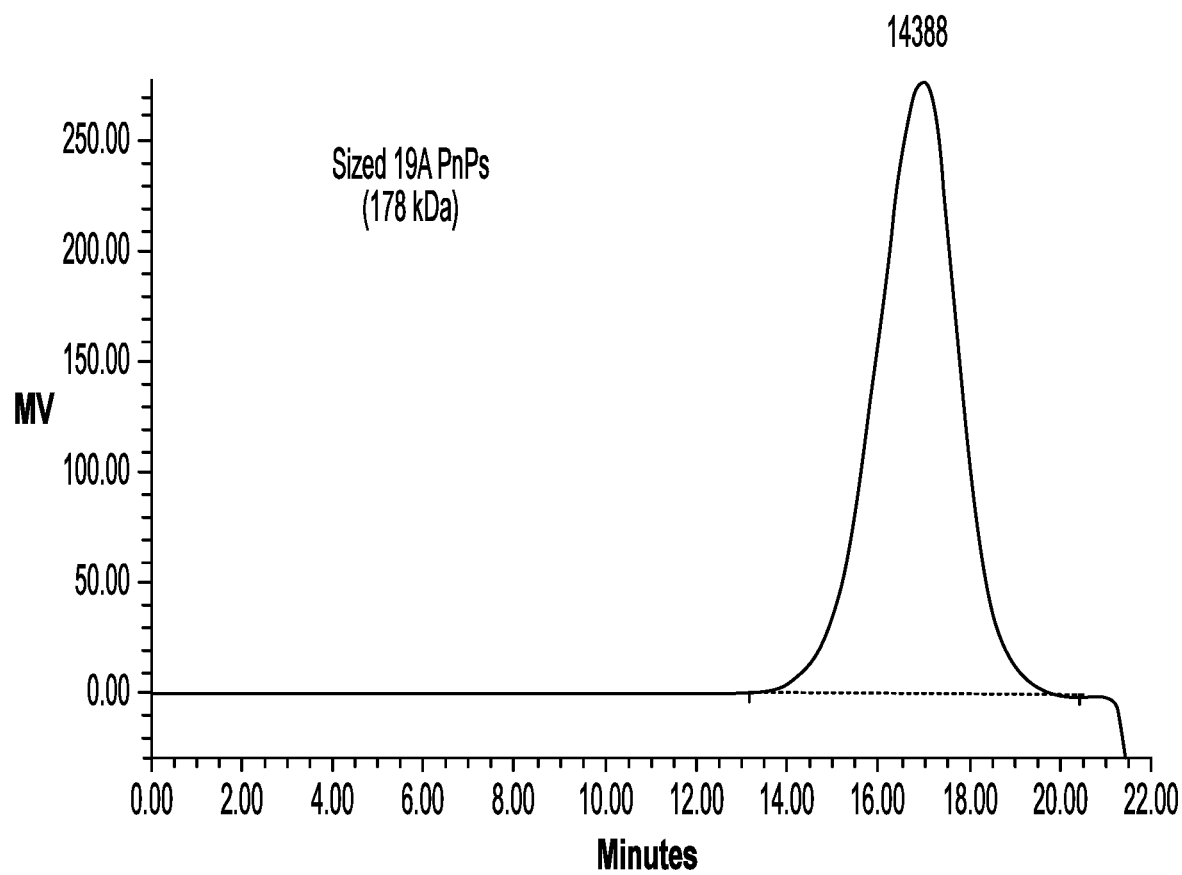
Figure 3B:
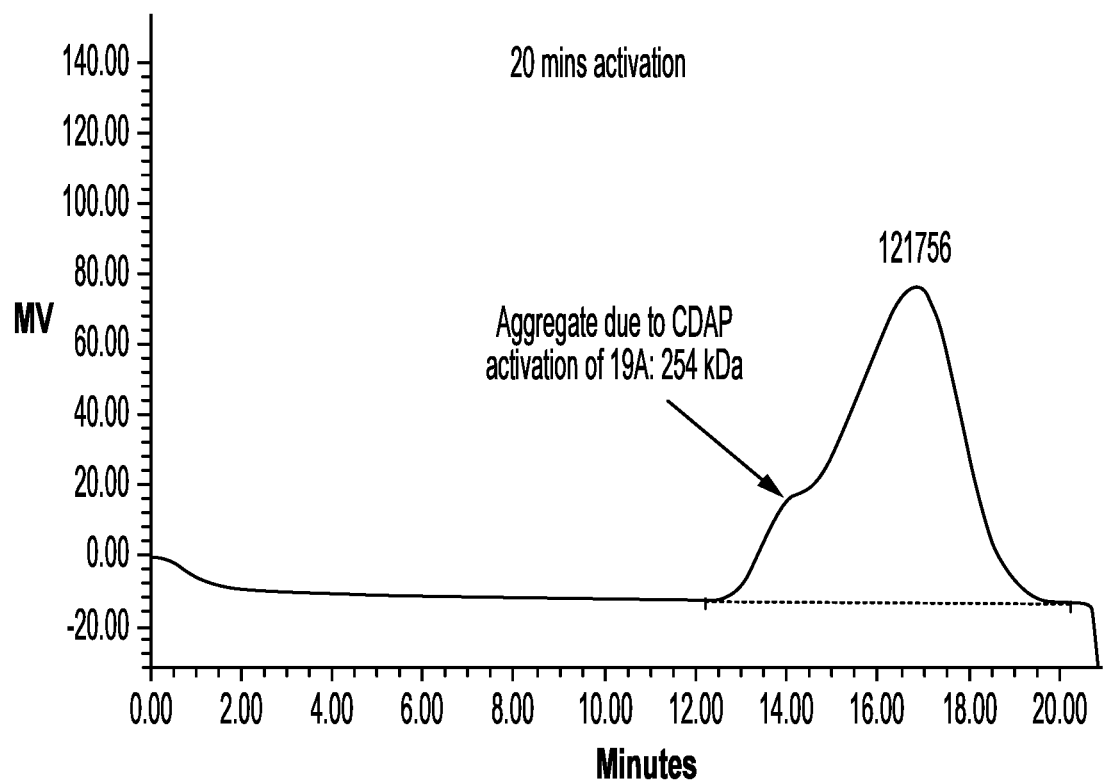
Figure 3C:
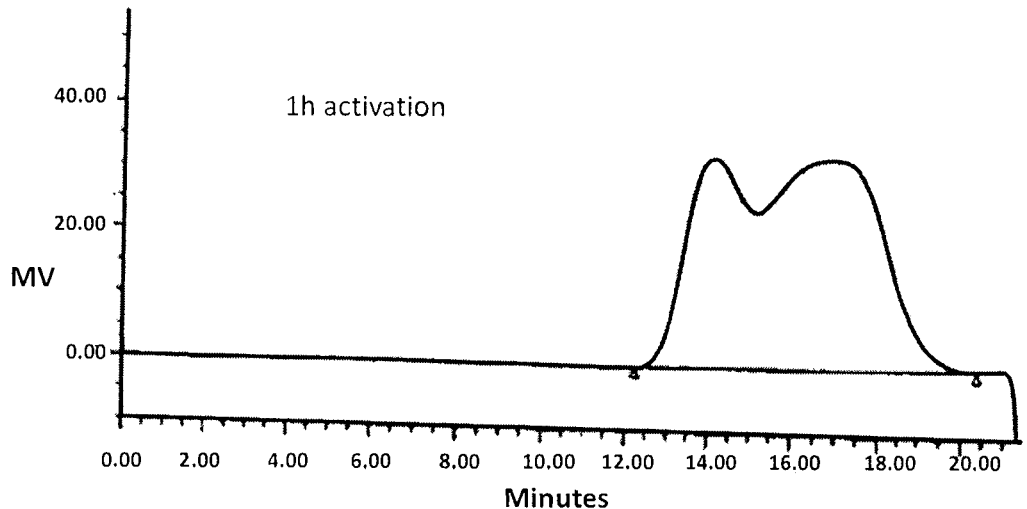
Figure 3D:
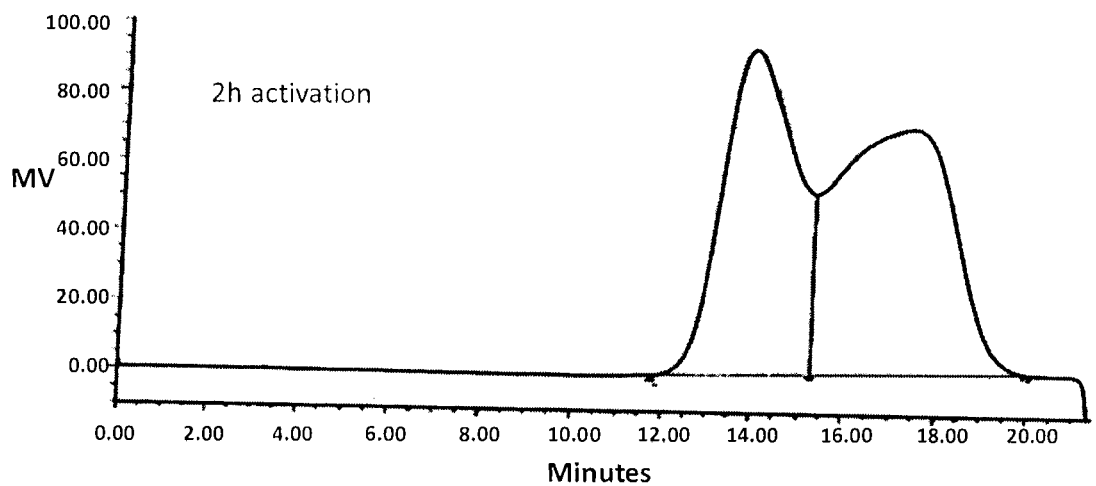
Figure 3E:
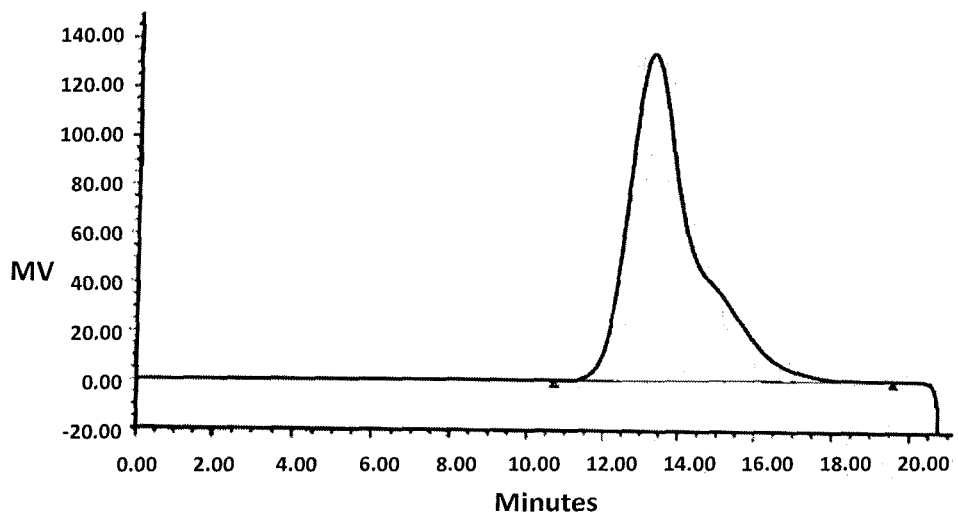
Figure 3F:
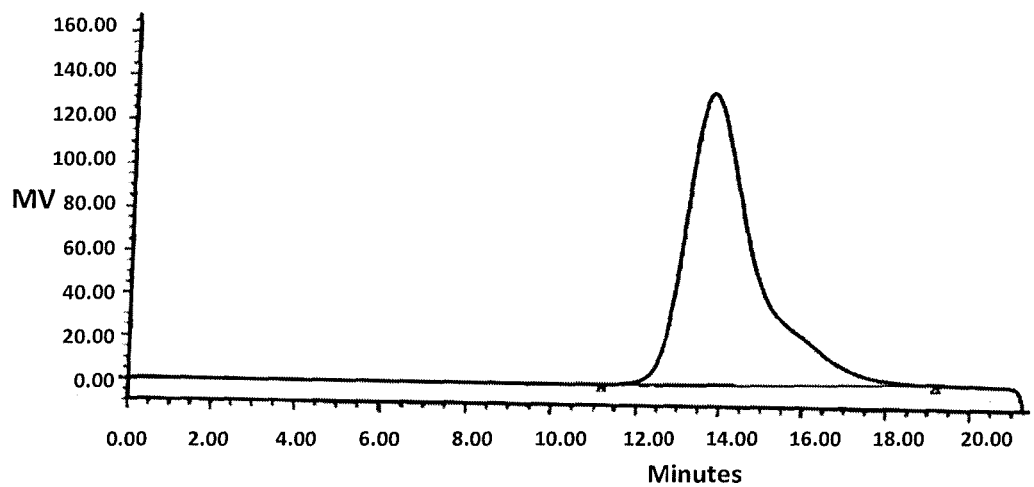
Figure 3G:
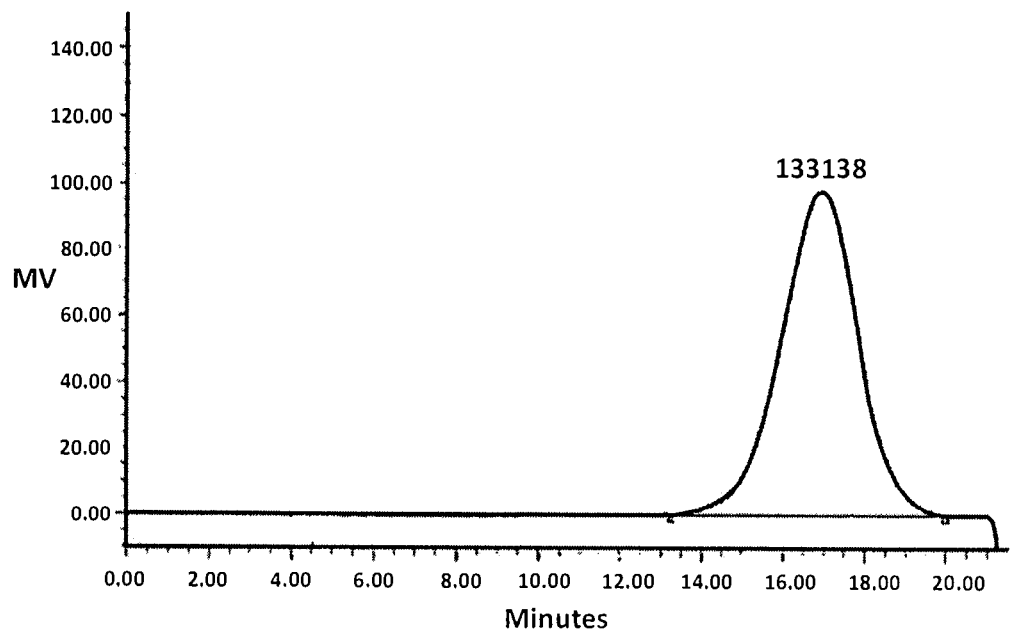
Figure 3H:
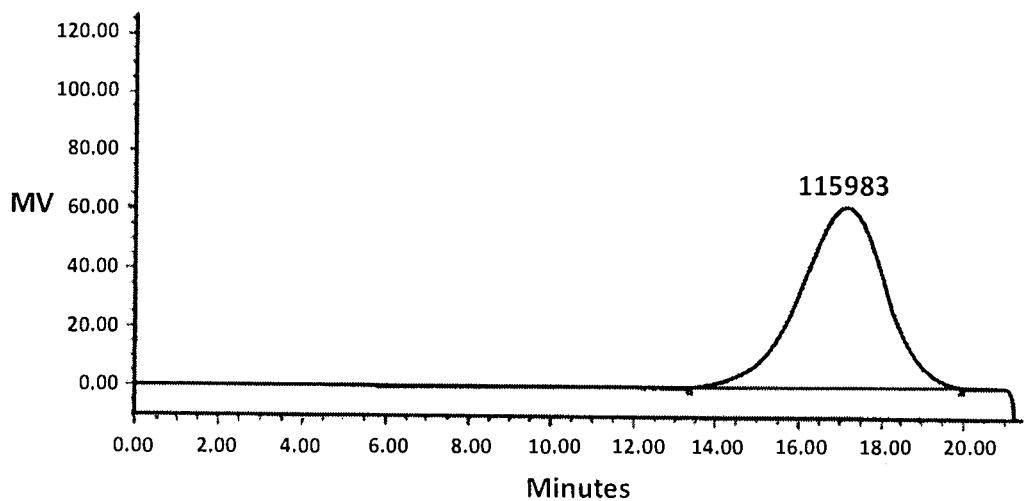
Figure 4A:
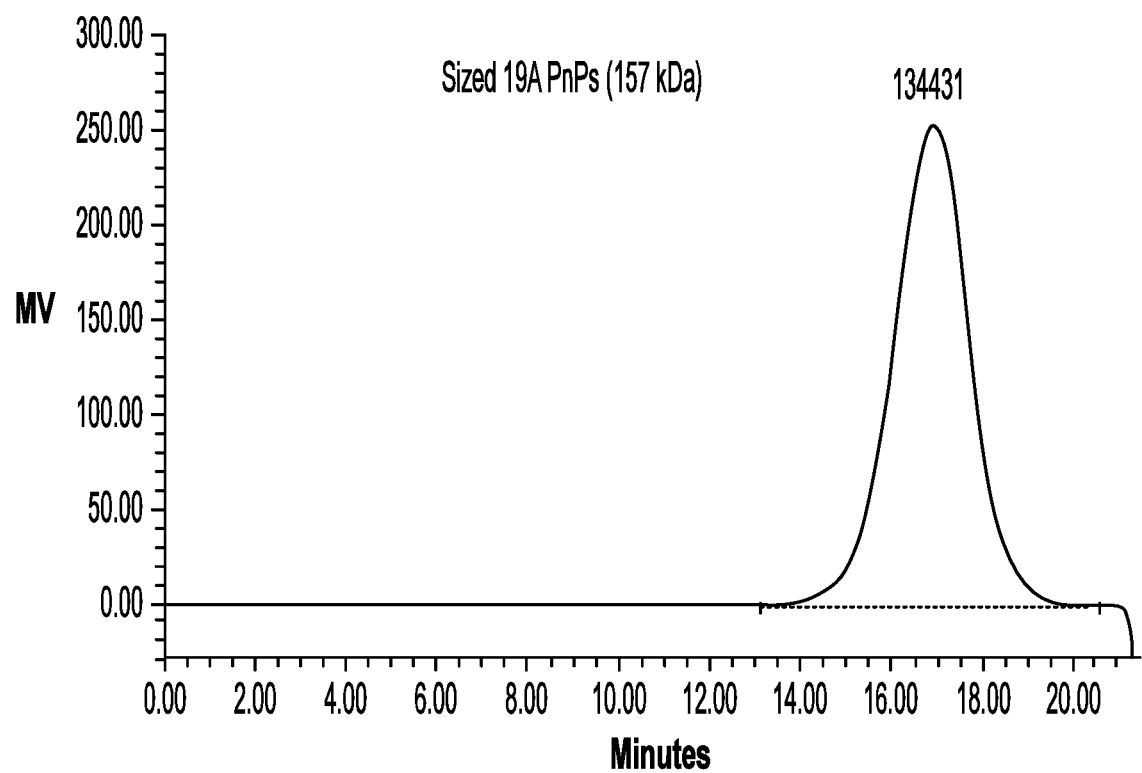
Figure 4B:
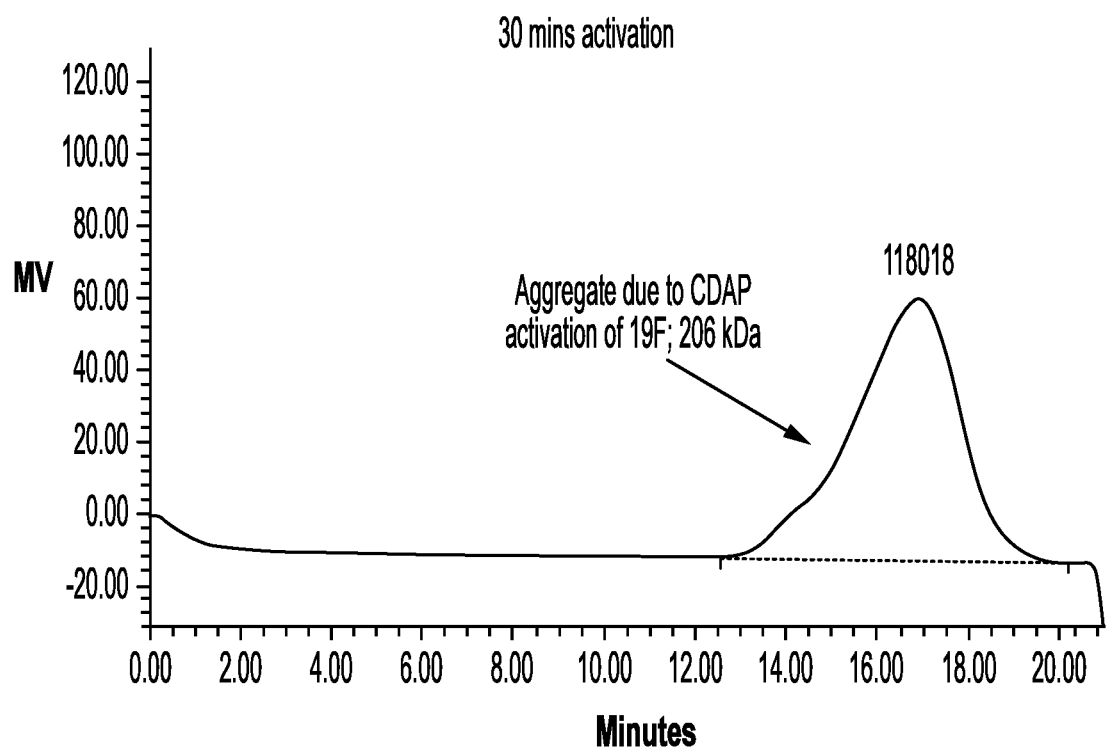
Figure 4C:
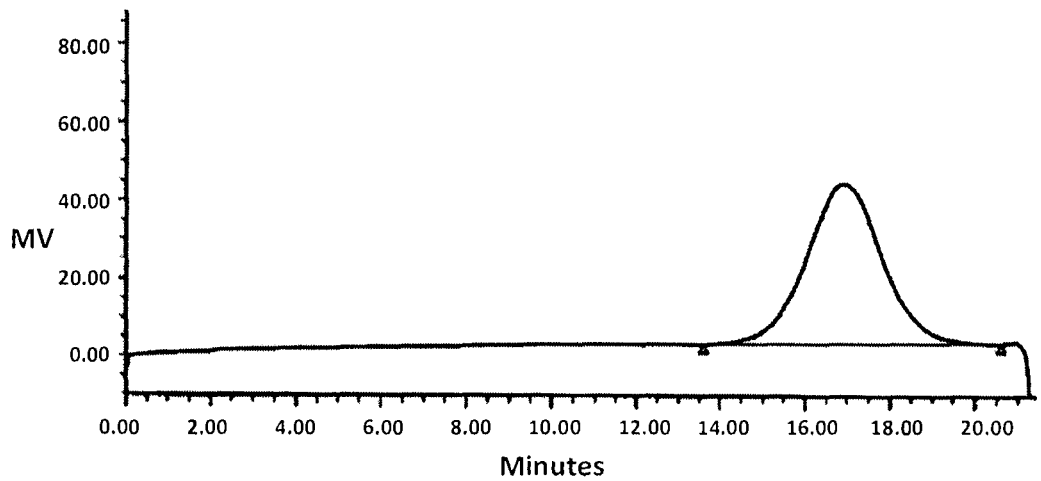
Figure 4D:
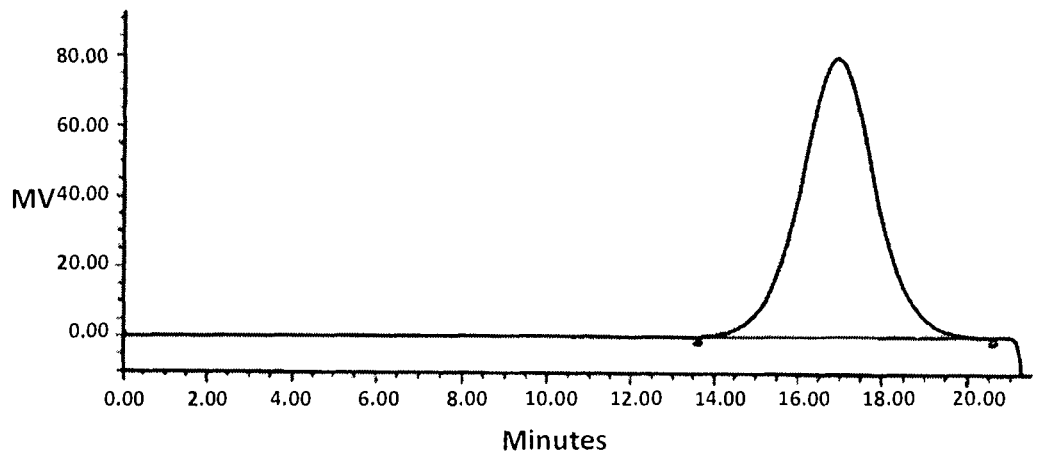

FIG. 1: SEC-HP-RI profile of sized 19A PnPs (178 KDa) before DMAP treatment FIG. 2: SEC-HP-RI profile of sized 19A PnPs (70 KDa) after 24 h (A) and 14.5 KDa after 72 h (B) DMAP treatment-degradation profiles FIG. 3: SEC-HP-RI profiles of sized 19A PnPs (178 KDa; A) and time-dependent aggregation of CDAP-mediated activated polysaccharides (3B, 3C & 3D),3E (conjugate without 10 KDa DF), 3F (conjugate with 10 KDa DF), 3G-sized 19A/3H-Activated 19A (modified Ps:CDAP ratio 1:1 for 19A) conjugation method without using 10 KDa diafiltration step.

FIG. 4: SEC-HP-RI profiles of sized 19F PnPs (157 KDa; A) and time-dependent aggregation of CDAP-mediated activated polysaccharides (B), 4C/4D (modified Ps:CDAP ratio 1:1 for 19F) conjugation method without using 10 KDa diafiltration step FIG. 5: Six bladed Rushton type turbine Flat Blade Impeller FIG. 6: Adsorption protocol

DETAILED DESCRIPTION

It is an object of the invention to provide improvements in the stability of vaccines which include aluminium salts and, in particular, methods for minimizing aggregation and improvements in percent adsorption of individual conjugates in a multivalent pneumococcal polysaccharide-protein conjugate vaccines. The inventors of present invention have observed that combined adsorption of polysaccharide-protein conjugates and use of polysaccharide to protein ratio greater than 1:1 results in i) percent adsorption of less than 55% for *S. pneumoniae* conjugates for Serotypes 6A, 9V and 23F and ii) percent adsorption from about 80% to 90% for remaining serotype conjugates, thereby failing to achieve complete adsorption for an individual serotype conjugate for a given multivalent pneumococcal conjugate formulation. Also it was observed that vaccine formulation prepared by using pH between 6.8 to 7.0 resulted in an aggregation of about 4 to 10% and lower adsorption.

The polysaccharide was cultivated using a method as described in Patent WO2013088448A1, wherein said method comprises (a) providing an inoculum of a strain of bacteria expressing the CP; (b) cultivating the strain by fermentation at pH 7.2, wherein the rate of feed medium addition is equivalent to the rate of alkali mixture addition for maintaining a preset pH; c) fermenting the culture medium at 35-38° C. under stirring at 50-150 RPM with an air flow rate of 0.1-0.5 vvm.

The polysaccharide was purified by the process described in Patent WO2012127485. Pn-Ps prepared by the instant process shows recovery of about 60 to 70%, wherein C-polysaccharide contamination reduction is of 1 to 5 fold as compared to the C-Ps content of post-Hydrophobic interaction chromatography (HIC) or pre ion exchange chromatography (IEC), protein contamination is less than 1% and nucleic acid contamination is less than 1%. The said process has been carried out at Research, Pilot and commercial scale.

This process can purify polysaccharides with 80-90% less time consumption & 90% less cost when compared with CTAB/Alcohol based methods.

According to one important embodiment of the instant invention, improved percent adsorption between 75 to 95% can be obtained for *S. pneumoniae* conjugates by i) employing polysaccharide to protein ratio of about 0.8 to 1.4 ii) utilizing individual or separate adsorption for poorly adsorbing *S. pneumoniae* conjugates, iii) keeping lower pH during formulation.

According to one aspect of first embodiment, preferred polysaccharide to protein ratio is 1:1.

According to a second aspect of first embodiment, said composition comprises of at least 2 polysaccharide protein conjugates having polysaccharide selected from serotypes 1, 2, 3, 4, 5, 6A, 6B, 7F, 8, 9V, 9F, 9N, 12F, 14, 15B, 17F, 18C, 19A, 19F, 20, 22F, 23F, 33F and 45

According to a third aspect of first embodiment, individual mode of adsorption can be utilized for any *S. pneumoniae* serotype selected from of 2, 3, 4, 6A, 8, 9V, 9F, 9N, 12F, 15B, 17F, 18C, 20, 22F, 23F, 33F and 45, preferably for *S. pneumoniae* serotypes 6A, 9V, and 23F.

According to a preferred aspect of first embodiment, the multivalent pneumococcal conjugate vaccine is 10 valent wherein *S. pneumoniae* serotypes 6A, 9V, and 23F are individually adsorbed as a separate blend and then added to another blend comprising of a mixture of *S. pneumoniae* serotypes 1, 5, 6B, 7F, 14, 19A and 19F that have been adsorbed in a combined mode.

According to another preferred aspect of first embodiment, the multivalent pneumococcal conjugate vaccine is 11, 13, 15, 16 or more valent wherein at least one *S. pneumoniae* serotype selected from a group of 2, 3, 4, 6A, 8, 9V, 9F, 9N, 12F, 15B, 17F, 18C, 20, 22F, 23F, 33F and 45 is individually adsorbed or adsorbed in a smaller group as a separate blend and then added to another blend comprising of a mixture of *S. pneumoniae* serotypes 1, 5, 6B, 7F, 14, 19A and 19F that have been adsorbed in a combined mode.

According to yet another preferred aspect of first embodiment, the multivalent pneumococcal conjugate vaccine is 16 valent wherein at least one S. pneumoniae serotype selected from a group of 2, 3, 4, 6A, 9V, 12F, 15B, 18C, and 23F is individually adsorbed or in smaller groups as a separate blend and then added to another blend comprising of a mixture of S. pneumoniae serotypes 1, 5, 6B, 7F, 14, 19A and 19F that have been adsorbed in a combined mode.

A second embodiment of the instant invention is that aggregation in a multivalent pneumococcal polysaccharide-protein conjugate formulation can be completely prevented by i) utilizing a pH shift from neutral pH to acidic pH and ii) use of histidine-succinic acid buffer combination.

According to one aspect of second embodiment, said pH shift can occur from 6.8 to a pH selected from but not limited to 5.2, 5.3, 5.4, 5.5, 5.6, 5.7, 5.8 and 5.9. More preferably from 6.8 to a pH selected from 5.4, 5.5, 5.6, 5.7 and 5.8.

According to another aspect of second embodiment, said Histidine-Succinic acid buffer system can have a concentration between 1 mM and 200 M. The concentration is preferably at least 1 mM (e.g. at most 200 mM, 150 mM, 100 mM, 90 mM, 80 mM, 70 mM, 60 mM, 50 mM, 40 mM, 30 mM, 20 mM, 10 mM etc.). More preferably the concentration of Histidine-Succinic acid buffer in the composition is between 10 mM and 40 mM.

A third embodiment of the instant invention is that floccules or aggregate formation in pneumococcal bulk conjugates can be prevented by utilizing a rushton turbine flat blade impellers instead of a magnetically stirred, axial and radial type impellers in formulation vessels.

The stability of an immunogenic composition of the invention is readily determined using standard techniques, which are well known and routine to those of skill in the art. For example, an immunogenic composition is assayed for percent adsorption of conjugates, stability, aggregation, immunogenicity, particulate formation, protein (concentration) loss, and the like, by methods including, but not limited to, ELISA, light scattering, optical density, sedimentation velocity centrifugation, sedimentation equilibrium centrifugation, circular dichroism (CD), Lowry assay, bicinchoninic acid (BCA) assay, and the like.

In a preferred embodiment, instant invention provides a novel ELISA that can directly quantify conjugated/bound polysaccharide without affecting antigenicity of conjugates in multivalent pneumococcal conjugate vaccines. The same can be utilized for quantification of unadsorbed conjugate content in formulation matrix as an indicating parameter for percent adsorption wherein the conjugates show more than 70% adsorption. Preferably, said ELISA can employ a pre-assay step involving desorption of conjugate from alum adjuvant without impacting the antigenicity of the carrier protein as well as the conjugated Polysaccharide. More specifically, the dissolution of alum adsorbed conjugate samples is achieved using sodium hydroxide and citric acid.

The carrier protein can be selected from a group of but not limited to CRM197, P4, diphtheria toxoid, tetanus toxoid, fragment C of tetanus toxoid, pertussis toxoid, protein D of H. influenzae, E. coli LT, E. coli ST, and exotoxin A from Pseudomonas aeruginosa, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11, protective antigen (PA) of Bacillus anthracis and detoxified edema factor (EF) and lethal factor (LF) of Bacillus anthracis, ovalbumin, keyhole limpet hemocyanin (KLH), human serum albumin, bovine serum albumin (BSA) and purified protein derivative of tuberculin (PPD), particularly CRM197 or P4.

According to a preferred embodiment, said multivalent composition can comprise of
i) at least one polysaccharide protein conjugate having CRM197 as carrier protein, at least one polysaccharide protein having TT as carrier protein; or
ii) at least one polysaccharide protein conjugate having CRM197 as carrier protein, at least one polysaccharide protein having DT as carrier protein; or
iii) at least one polysaccharide protein conjugate having CRM197 as carrier protein, at least one polysaccharide protein having pneumococcal surface adhesin A (PsaA) as carrier protein; or
iv) at least one polysaccharide protein conjugate having CRM197 as carrier protein, at least one polysaccharide protein having TT as carrier protein, at least one polysaccharide protein having DT as carrier protein; or
v) at least one polysaccharide protein conjugate having CRM197 as carrier protein, at least one polysaccharide protein having TT as carrier protein, at least one polysaccharide protein having pneumococcal surface adhesin A (PsaA) as carrier protein; or
vi) at least one polysaccharide protein conjugate having CRM197 as carrier protein, at least one polysaccharide protein having DT as carrier protein, at least one polysaccharide protein having pneumococcal surface adhesin A (PsaA) as carrier protein.

In another embodiment, the preferred carrier protein conjugated to Serotype 3 is CRM-197, Serotype 4 is TT or DT and Serotype 18C is CRM197.

Another embodiment of the present invention includes the use of PsaA as a carrier protein in the final formulation. The PsaA can also be used in the final formulation as an adjuvant.

In certain embodiments, multivalent formulation of instant invention can comprise of a surfactant preferably polysorbate 20. In certain embodiments, the final concentration of the polysorbate 20 in formulation is 0.01% to 10% polysorbate 20 weight/volume of the formulation. In yet other embodiments, the final concentration of the polysorbate 20 in the formulation is 0.01% polysorbate 20 weight/volume of the formulation. In other embodiments, the final concentration of the polysorbate 20 in the formulation is 0.05% polysorbate 20 weight/volume of the formulation. In yet other embodiments, the final concentration of the polysorbate 20 in the formulation is 0.1% polysorbate 20 weight/volume of the formulation. In another embodiment, the final concentration of the polysorbate 20 in the formulation is 1.0% polysorbate 20 weight/volume of the formulation. In yet another embodiment, the final concentration of the polysorbate 20 in the formulation is 10.0% polysorbate 20 weight/volume of the formulation.

The present multivalent vaccine formulations can comprise of preservatives selected from a group of but not limited to mercurial preservatives (e.g. thimerosal), 2-phenoxy-ethanol, methyl parabens, propyl parabens and benzyl alcohol (or mixtures thereof).

According to a preferred embodiment of present invention, said multivalent pneumococcal polysaccharide-protein conjugate vaccine formulation, preferably 10 or 16 valent can comprise of aluminium phosphate adsorbed conjugates, Histidine, Succinic acid, Sodium chloride, Polysorbate 20 and thiomersal.

The vaccine composition of instant invention can comprise of a step of adding aluminium salt adjuvant at an amount of 20-375 µg, 20-300 µg, 20-200 µg, 25-150 µg of Al+++ per 0.5 ml dose.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. injection, subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications needles, and hyposprays. Dosage treatment may be a single dose schedule or a multiple dose schedule (e.g. including booster doses).

Preferably, the vaccines of the present invention may be stored in solution or lyophilized, wherein the lyophilized vaccine composition of the instant invention can be given as 1, 5 or 10 dose formulation with a diluent containing aluminium phosphate gel and NaCl.

Figure 5:
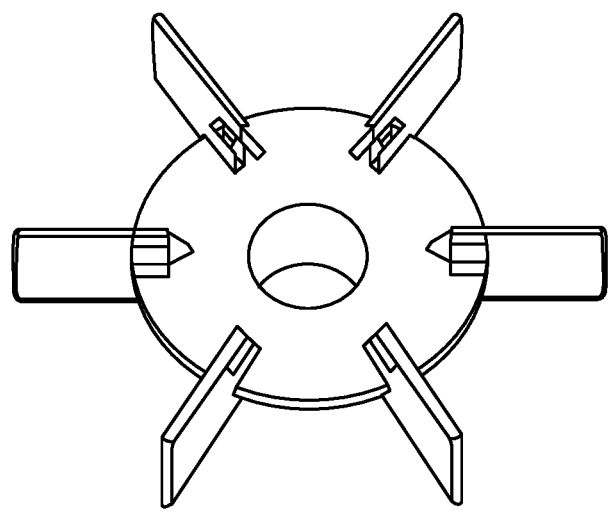
Figure 6:
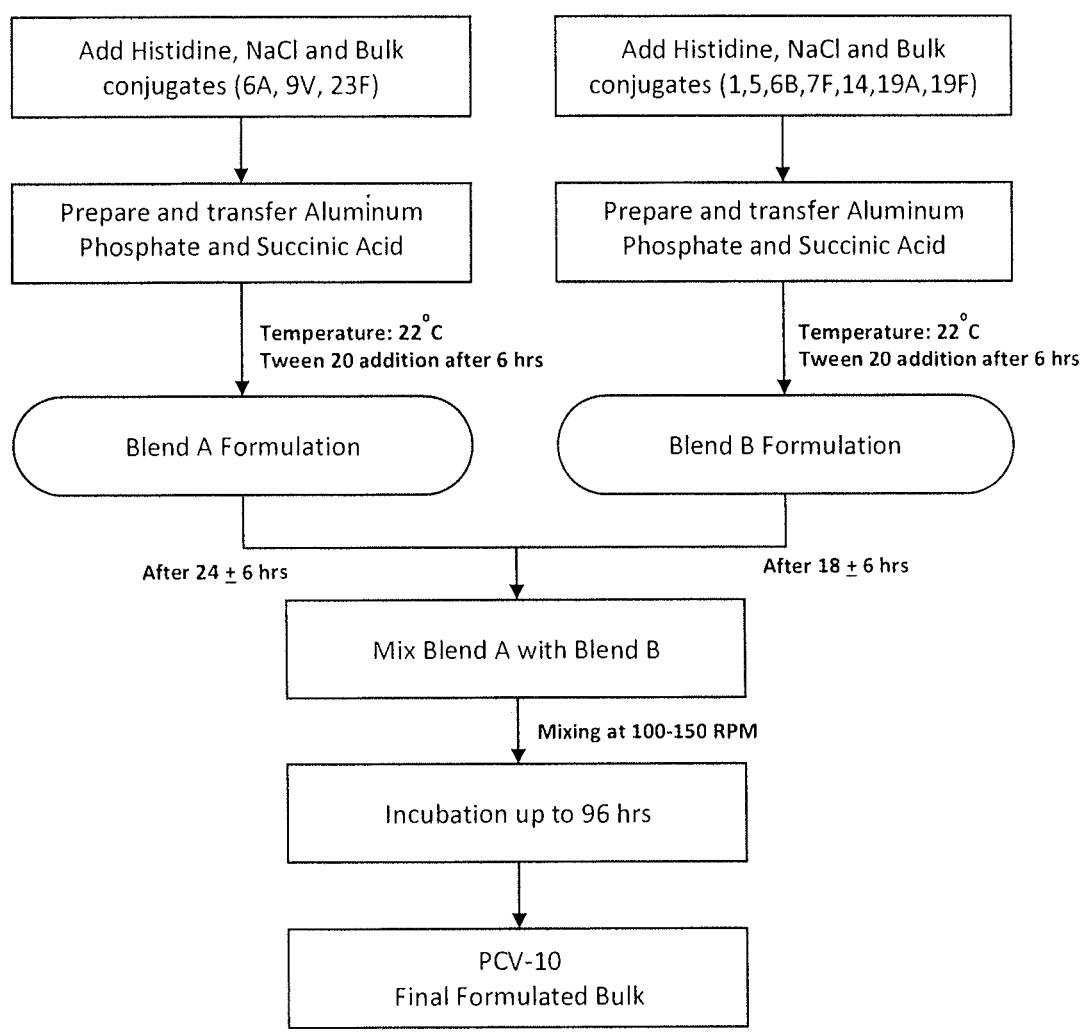

Another embodiment of the present invention includes the use of Rushton Turbine Flat Blade Impeller in the formulation vessel (Refer FIG. 5).

EXAMPLES

Example 1: Fermentation

Method comprises (a) providing inoculum of a strain of bacteria expressing the CP; (b) cultivating the strain by fermentation at pH 7.2, wherein the rate of feed medium addition is equivalent to the rate of alkali mixture addition for maintaining a preset pH; c) fermenting the culture medium at 35-38° C. under stirring at 50-150 RPM with an air flow rate of 0-0.5 vvm.

Example 2: Capsular Polysaccharide Purification

S. Pneumoniae Capsular Polysaccharide Serotype 19F Purification (HIC followed by IEC)

5 L clarified broth from the fermenter cultures of S. pneumoniae serotype 19F was concentrated and diafiltered to 500 ml using a 100 KDa MWCO membrane. Diafiltration was accomplished using 25 mM sodium phosphate buffer at neutral pH followed by diafiltration with water for injection (WFI).

Nuclease was added to the polysaccharide solution to achieve a final concentration of 8 U/ml of solution. The enzyme treatment was carried out at 370 C, for 10±2 hrs with stirring.

Ammonium sulphate was added to the nuclease treated polysaccharide solution to 50% saturation and incubated at 2-8° C. for 12±2 hrs (except serotypes 5 and 4). The mixture was subjected to centrifugation. The pellet (precipitate) was discarded. The solution (~500 ml) is subjected to 100 kD diafiltration using NaCl followed by chilled WFI. This diafiltered solution containing polysaccharide with a buffer and high salt concentration was loaded on HIC column.

The hydrophobic interaction chromatography column (300 ml) was equilibrated with 50% saturated ammonium sulphate buffer and the polysaccharide solution (500 ml) was then loaded onto the column in pH range 6 to 8, preferably at pH 6 to 7 pH. The column was further washed with the buffer containing 50% saturated ammonium sulphate. Under these conditions, the polysaccharide was recovered in the flow-through and equilibration wash from the column.

The polysaccharide solution was then concentrated using a 100 KDa MWCO filter and then diafiltered with NaCl and Water for Injection (WFI).

The ion exchange chromatography column (300 ml) (strong anion exchanger) was equilibrated with 20 mM sodium phosphate buffer and the polysaccharide solution (500 ml) was then loaded onto the column in pH range 6 to 8, preferably at pH 6.5 to 7.5 pH. The column was further washed with buffer. The adsorbed polysaccharides were eluted with step gradient elution using 1.0 M NaCl (various polysaccharides were eluted at different ionic strengths of NaCl).

The polysaccharide solution was then concentrated using a 100 KDa MWCO filter and then diafiltered with Water for Injection (WFI).

The diafiltered polysaccharide solution was filtered through a 0.22µ membrane filter into polypropylene bottles. The purified polysaccharide was stored frozen at −20±50C.

The above process was also utilized for serotypes 4, 6A, 6B, 7F, 9V, 10A, 14, 18C, 19A, 19F, & 23F.

Results:

C-Polysaccharide post HIC & post Ion exchange chromatography was estimated by H1/P31 NMR spectra. The process resulted in 2-3 fold reduction in contaminants content.

Example 3: Sizing of Polysaccharides

A homogenizer (Microfluidics) apparatus was used to reduce the molecular weight of the polysaccharide before the activation step. For 19A size reduction was done at 24-28 KPSI, whereas for 19F size reduction was done at 26-30 KPSI wherein the number of passes was about 1 to 3. The sized polysaccharide was diafiltered and concentrated followed by 0.22µ, filtration. The sized polysaccharide was then subjected to HPSEC-RI for estimation of average molecular weight.

Example 4: General Conjugation Process

Conjugation of polysaccharide to carrier protein was carried out using CDAP conjugation method of Lees et al (Vaccine 26: 190-198, 1996). Mechanically size reduced polysaccharides (except for 6A which was used in native form or sized depending on size of 6A) were dissolved in NaCl 2M. CDAP (in acetonitrile) from a 100 mg/ml stock solution was added to the polysaccharide solution as per polysaccharide:CDAP ratio. Approximate 1 minute later, 2M NaOH was added to obtain the specific activation pH. The activation of the polysaccharide was performed at this pH during 4-10 minutes at 22° C. CRM-197 (the quantity depend on initial Ps/Protein ratio) was added to the activated polysaccharide and the coupling reaction was performed at the specific pH for 3-8 hr depending on serotype. The reaction was then quenched with glycine for 1 hr at 220 C, and overnight at 120 C. The conjugates were then purified by 300 kDa to 500 kDa diafilteration followed by 100 kDa diafilteration. Further the polysaccharide and protein content of the purified 0.22 um filtered conjugates were determined.

TABLE 1

Serotype specific conjugation reaction parameter variations for 10 serotypes:
Conjugation Details for 10 serotypes

| Characteristics | Process conditions of different Serotypes | | | | | | | | | |
|---|---|---|---|---|---|---|---|---|---|---|
| | 1 | 5 | 6A | 6B | 7F | 9V | 14 | 19A | 19F | 23F |
| Ps conc. (mg/ml) | 4.5 | 5 | 5 | 11 | 10 | 8 | 10 | 9.5 | 9.5 | 9 |
| Ps dissolution | 2M NaCl | 2M NaCl | 2M NaCl | 2M NaCl | 2M NaCl | 2M NaCl | 2M NaCl | 2M NaCl | 2M NaCl | 2M NaCl |
| Activation time (min) | 4 | 4 | 4 | 4 | 4 | 4 | 4 | 4 | 10 | 4 |
| Ps/CDAP ratio | 1:1.25 | 1:1 | 1:1 | 1:1.15 | 1:1.25 | 1:1.2 | 1:1.1 | 1:1 | 1:0.8 | 1:1.1 |
| CRM 197 conc. (mg/ml) | 20 | 20 | 20 | 20 | 20 | 20 | 20 | 20 | 20 | 20 |
| Ps/CRM ratio | 0.82 | 0.75 | 1.05 | 0.77 | 0.85 | 0.87 | 0.82 | 0.86 | 0.96 | 0.71 |
| $pH^a$:$pH^c$:$pH^q$ | 9.5:9.5:9.5 | 9.5:9.5:9.5 | 9.5:9.5:9.5 | 9.5:9.5:9.5 | 9.5:9.5:9.5 | 9.5:9.5:9.5 | 9.5:9.5:9.5 | 09:09:09 | 9.5:9.5:9.5 | 9.5:9.5:9.5 |
| Free Ps (%) | <1 | 6.3 | 2.63 | 1.57 | <1 | ND | 2.53 | 1.5 | 1.07 | 2.59 |
| Free protein (%) | ND | 1.54 | 2.2 | ND | ND | ND | ND | ND | 2.2 | ND |
| Mol. Size Distribution (%) | 70.56 | 74.93 | 67.67 | 76.52 | 75.68 | 72.75 | 76.59 | 78.1 | 74.35 | 72.91 |

TABLE 2

Comparison in percent adsorption of individual serotypes of PCV-10 formulations in one-and two-blend approach of formulation process.

| | | One blend approach (all antigen together) % Adsorption | | | Two blend approach (Blend A and B) % Adsorption | | |
|---|---|---|---|---|---|---|---|
| S. No. | Serotypes of PCV-10 Formulations | Exp-1 | Exp-2 | Exp-3 | Exp-4 | Exp-5 | Exp-6 |
| 1 | Serotype 1 | 90 | 85 | 92 | >99 | >99 | 97 |
| 2 | Serotype 5 | 84 | 82 | 85 | 90 | 88 | 97 |
| 3 | Serotype 6A | 67 | 51 | 61 | 77 | 71 | 93 |
| 4 | Serotype 6B | 82 | 72 | 83 | 84 | 80 | 86 |
| 5 | Serotype 7F | 83 | 77 | 81 | 87 | 86 | 84 |
| 6 | Serotype 9V | 67 | 43 | 74 | 89 | 85 | 85 |
| 7 | Serotype 14 | 86 | 83 | 88 | 92 | 91 | 90 |
| 8 | Serotype 19A | 95 | 92 | 97 | 95 | 93 | 85 |
| 9 | Serotype 19F | 91 | 87 | 93 | 91 | 88 | 75 |
| 10 | Serotype 23F | 56 | 52 | 58 | 84 | 81 | 81 |

In one blend approach the serotypes 6A, 9V, and 23F were poorly adsorbed in the formulation, whereas for the two blend approach the percent adsorption was >70% for all serotypes.

TABLE 3

Effect of pH shift on aggregation behavior of PCV-10 formulations

| S. No. | Formulation Descriptions | % Vials rejection due to aggregates (white particles/floccules) | | |
|---|---|---|---|---|
| | | Experiment-7 | Experiment-8 | Experiment-9 |
| 1 | PCV-10 Formulations without 'pH shift' | 10% | 4% | 6% |
| 2 | PCV-10 Formulations with 'pH shift' from pH 6.8 to pH 5.6-5.8 | Experiment-10 No aggregate (no screening rejection) | Experiment-11 No aggregate (no screening rejection) | Experiment-12 No aggregate (no screening rejection) |

No aggregates were found for the pH 5.6-5.8 for PCV10 formulation when compared with that of pH 6.8.

The polysaccharide to protein ratio (1:1) was found to have advantageous effect on the extent of adsorption of Pneumococcal conjugate in formulation.

TABLE 4

Effect of Ps to $CRM_{197}$ ratio on adsorption of pneumococcal conjugate (serotype 6A) in Formulation

| S. No. | Pneumococcal conjugate serotype 6A bulk | Ps to Protein Ratio | Adsorption (%) |
|---|---|---|---|
| 1 | ZPN6ACP1201 | 1.95 | 34 |
| 2 | ZPN6ACP1203 | 1.51 | 42 |
| 3 | ZPN6ACP1204-A | 1.32 | 87 |
| 4 | ZPN6ACP1204-B | 1.15 | 95 |
| 5 | ZPN6ACP1205 | 1.09 | 86 |

The effect of polysaccharide to protein ratio was observed on adsorption of conjugates. 6A conjugates which had Ps to protein ratio of >1.5 showed poor adsorption. Most of the serotypes used in the PCV-10 formulation contained Ps: Pr ratio in the range of 0.6-1.3 which resulted in optimum adsorption of various serotypes including serotype 6A. Based on the adsorption data achieved for 6A serotype and PCV-10 formulation experience, while formulating 16 valent it can be extrapolated that Ps:Pr ratio of remaining 6 conjugates in the similar range could ensure consistent adsorption of all 16 serotype conjugates.

TABLE 5

Specifications of Rushton Turbine Flat Blade Impeller for different vessels

| | |
|---|---|
| Geometric Volume (L) | 14 |
| Working Volume (L) | 10.0 |
| Blade Diameter (mm) | 74.7 |
| Blade Height (mm) | 17.3 |
| Number of Blades | 6 |
| Agitation control (rpm) | 50-500 |
| Tip Speed (m/s) | 0.19-1.95 |

Example 6: ELISA Protocol

Antigen content and percent adsorption was determined using modified Sandwich ELISA.

The conventional Sandwich ELISA has been modified with respect to following test conditions/assay conditions and thereby has following advantageous attributes—
  i. to quantify conjugated Polysaccharide in the presence of 9 other conjugated antigens in a 10 valent vaccine ii. to elute all ten conjugate from aluminum phosphate gel where adsorption is more than 80%
iii. wherein capture of conjugate occurs even if it is at pH 9 without damaging the conjugate antigenicity Antigen content and percent adsorption was determined using ELISA as per the protocol given below:

Day 1

1. The plates were coated with Capture Antibody (anti-carrier protein antibody) followed by incubation for 0.5-2 hrs at 35±5° C.
2. plates were washed 3-6 times using ELISA plate washer
3. plates were blocked with blocking buffer (3% BSA in 1×PBS and tris buffer for serotypes 14 and 9V) followed by incubation for 1.5-2.5 hrs at 30±5° C.
4. plates were washed 3 times using ELISA plate washer
5. samples were added into the plates
6. plates were incubated overnight at 5±3° C.

Day 2

1. plates were allowed to attain room temperature
2. primary antibody was added after washing of the plates 3 times followed by incubation at RT for 25±2 for 30 mins followed by washing.
3. secondary antibody was added and followed by incubation at 25±2 for 30 minutes.
4. substrate TMB was added followed by incubation at RT for 15-20 mins in dark
5. stop solution was added
6. plates were read at 450 nm.

Procedure for Dissolution of Sample without Harming the Epitope of Carrier Protein An appropriate quantity of 0.5 M-2M NaOH was added to 2 ml of vaccine sample. Said sample was subjected to vortex gently until the solution became clear. The pH of the solution was adjusted from 9-12 till the solution became clear. pH of the solution was brought back to 6-7.4 using 0.5M to 2M citric acid. Said solution was subjected to centrifugation (dissolved samples) at 3000 to 6000×g for 5 min and supernatant was collected for the testing.

TABLE 6

|  | Batch 1 | | Batch 2 | |
| --- | --- | --- | --- | --- |
| Serotype | Content in µg/ml | % Adsorption | Content in µg/ml | % Adsorption |
| Serotype 1 | 3.87 | 89 | 4.66 | 99.4 |
| Serotype 5 | 3.57 | 83 | 4.03 | 90.8 |
| Serotype 6A | 3.39 | 83 | 4.6 | 68.3 |
| Serotype 6B | 8.01 | 80 | 6.8 | 85 |
| Serotype 7F | 4.72 | 97 | 4.18 | 84.4 |
| Serotype 9V | 4.61 | 80 | 3.95 | 70.4 |
| Serotype 14 | 5.11 | 94 | 5.06 | 92.5 |
| Serotype 19A | 4.42 | 94 | 3.65 | 91.8 |
| Serotype 19F | 4.35 | 82 | 4.14 | 81.4 |
| Serotype 23F | 3.66 | 72 | 4.03 | 75 |

Example 7: Pneumococcal Conjugate Vaccine—10 Valent (PCV10)

TABLE 7

PCV10 composition:

| Sr. No | Name of the ingredient | Quantity/dose(0.5 ml) |
| --- | --- | --- |
| 1 | Polysaccharide Serotype 1, 5, 6A, 7F, 9V, 14, 19A, 19F and 23F* | 2 µg each |
| 2 | Polysaccharide Serotype 6B* | 4 µg |
| 3 | Adju-Phos ® Aluminium phosphate | 0.125 mg as Al$^{+++}$ |
| 4 | Sodium Chloride | 4.5 mg |
| 5 | Succinic acid | 1.18 mg |
| 6 | Polysorbate-20 | 50 µg |
| 7 | Thiomersal (only for multidose presentation) | 25 µg |
| 8 | L-Histidine | 1.55 mg |

*Active ingredients are conjugated with Carrier protein CRM197

Example 8: Formulation 1 (PCV16)

Pneumococcal Conjugate Vaccine—16 Valent (PCV16)

TABLE 8

PCV16 composition "I"

| S. No. | Compositions | Quantity/dose |
| --- | --- | --- |
| | Active Ingredients* | |
| 1 | Serotype 1 | 2.0 µg |
| 2 | Serotype 2 | 2.0 µg |
| 3 | Serotype 3 | 2.0 µg |
| 4 | Serotype 4 | 2.0 µg |
| 5 | Serotype 5 | 2.0 µg |
| 6 | Serotype 6A | 2.0 µg |
| 7 | Serotype 6B | 4.0 µg |
| 8 | Serotype 7F | 2.0 µg |
| 9 | Serotype 9V | 2.0 µg |
| 10 | Serotype 12F | 2.0 µg |
| 11 | Serotype 14 | 2.0 µg |
| 12 | Serotype 15B | 2.0 µg |
| 13 | Serotype 18C | 2.0 µg |
| 14 | Serotype 19A | 2.0 µg |
| 15 | Serotype 19F | 2.0 µg |
| 16 | Serotype 23F | 2.0 µg |
| | Inactive Ingredients | |
| 17 | Aluminium phosphate | NMT 1.25 mg of Al$^{3+}$ |
| 18 | Histidine | 1.55 mg |
| 19 | Carrier proteins | 11.3-113.3 µg |
| 20 | Succinic acid | 1.18 mg |
| 21 | Sodium Chloride | 4.5 mg |
| 22 | Polysorbate 20 | 50 µg |
| 23 | Thiomersal** | 25 µg |
| 24 | WFI | q.s. |

*The active ingredients of the vaccine are conjugated to atleast one carrier protein selected from CRM197, TT and DT.
**Added only in multi-dose presentation

Example 9: Formulation 1 (PCV16)

TABLE 9

PCV16 composition "II"

| S. No. | Compositions | Quantity/dose |
|---|---|---|
| | Active Ingredients* | |
| 1 | Serotype 1 | 2.0 µg |
| 2 | Serotype 2 | 2.0 µg |
| 3 | Serotype 3 | 2.0 µg |
| 4 | Serotype 4 | 2.0 µg |
| 5 | Serotype 5 | 2.0 µg |
| 6 | Serotype 6A | 2.0 µg |
| 7 | Serotype 6B | 4.0 µg |
| 8 | Serotype 7F | 2.0 µg |
| 9 | Serotype 9V | 2.0 µg |
| 10 | Serotype 12F | 2.0 µg |
| 11 | Serotype 14 | 2.0 µg |
| 12 | Serotype 15B | 2.0 µg |
| 13 | Serotype 18C | 2.0 µg |
| 14 | Serotype 19A | 2.0 µg |
| 15 | Serotype 19F | 2.0 µg |
| 16 | Serotype 23F | 2.0 µg |
| | Inactive Ingredients | |
| 17 | Aluminium phosphate | NMT 1.25 mg of $Al^{3+}$ |
| 18 | Histidine | 1.55 mg |
| 19 | Carrier proteins | 11.3-113.3 µg |
| 20 | Succinic acid | 1.18 mg |
| 21 | Sodium Chloride | 4.5 mg |
| 22 | Polysorbate 20 | 50 µg |
| 23 | 2-Phenoxy Ethanol** | 10 mg |
| 24 | WFI | q.s. |

*The active ingredients of the vaccine are conjugated to atleast one carrier protein selected from CRM197, TT and DT.
**Added only in multi-dose presentation

Example 10

I) Degradation of Sized PnPs (19A, 19F, 6A and 6B) in Presence of DMAP:

Sized PnPs in reaction solution was treated with DMAP in a ratio of 1:1.5 and checked for its degradation profile by SEC-HP-RI.

Results:

It was observed that only 19A PnPs undergoes degradation in presence of DMAP whereas other phosphodiester containing PnPs (19F, 6A & 6B) remain intact. Refer FIGS. 1 (without DMAP) & 2 which show the DMAP-mediated degradation of PnPs.

To minimize such degradation of 19A, activated PnPs was subjected to 10 KDa diafiltration using 2M NaCl to remove the DMAP formed from reaction solution before conjugation with $CRM_{197}$.

II) Degradation and Aggregation of Sized PnPs (19A, 19F, 6A and 6B) in Presence of CDAP:

Sized PnPs in reaction solution was treated with CDAP in the ratio of 1:1.5 during activation. It was observed that 50% DMAP is generated as by-product (measured by RP-HPLC) which leads to degradation of PnPs as well as aggregation between activated PnPs after certain time of activation (refer Table 2) Degradation and aggregation was checked by SEC-HP-RI profile. Refer FIGS. 3A (without CDAP), 3B, 3C & 3D (for 19A) & 4A (without CDAP) 4B (for 19F) which show the CDAP-mediated aggregation & degradation of PnPs.

TABLE 10

Factors responsible for polysaccharide-polysaccharide cross linking & aggregation
Effect of "duration of CDAP activation" on formation of "polysaccharide-polysaccharide aggregates"

| Serotypes | Mw of sized/ modified PnPs (KDa) [SEC-HP-RI] | Activated modified PnPs (KDa) [SEC-HP-RI] | Effects |
|---|---|---|---|
| 6A | 432 | 435 | No aggregation between activated polysaccharides |
| 6B | 131 | 131 | No aggregation between activated polysaccharides |
| 19A | 178 | 254 (after 20 min) | Aggregation between activated polysaccharides |
| | | 487 (after 60 min) | Aggregation between activated polysaccharides |
| | | 1173 (after 120 min) | Aggregation between activated polysaccharides |
| 19F | 157 | 205 (after 30 min) | Aggregation between activated polysaccharides |

III) Prevention of Degradation and Aggregation of Sized PnPs (19A and 19F) Having PnPs:CDAP of 1:1.5 by Employing Diafiltration Step:

To minimize such degradation and aggregation of 19A, activated PnPs was subjected to 10 KDa diafiltration using 2M NaCl to remove the DMAP formed from reaction solution before conjugation with $CRM_{197}$. Refer FIGS. 3E (conjugate without 10 KDa DF) & 3F (conjugate with 10 KDa DF) which shows the SEC-HP-RI profile of conjugate using 10 KDa diafiltered activated PnPs and $CRM_{197}$. However diafilteration step was adversely affecting conjugate yield resulting in a 30%-40% decrease in overall yield.

IV) Prevention of Degradation and Aggregation of Sized PnPs (19A and 19F) by Reducing Ratio of PnPs:CDAP to 1:1 (19A) and 1:0.8 (19F) without Employing Diafiltration Step Sized PnPs in reaction solution was treated with CDAP in the ratios of 1:1 and 1:0.8 for 19A and 19F respectively and checked for its degradation and aggregation profile by SEC-HP-RI.

Results:

It was observed that modified Ps:CDAP ratios (1:1 for 19A and 1:0.8 for 19F) were found to prevent degradation and aggregation for both 19A and 19F PnPs. Refer FIGS. 3 (G & H for 19A) & 4 (C & D for 19F). An additional advantage of using modified ratios was that it was devoid of a 10 KDa diafiltration step thus ensuring minimum loss in overall yield.

It was observed that in case of serotype 19A, when "duration of CDAP activation" was more than 10 min, it was resulting in cross linking of activated polysaccharide to activated polysaccharide ultimately leading to formation of "polysaccharide-polysaccharide aggregates".

Further in case of serotype 19F, when "duration of CDAP activation" was more than 20 min, it was resulting in cross linking of activated polysaccharide to activated polysaccharide ultimately leading to formation of "polysaccharide-polysaccharide aggregates". Further the duration of conjugation reaction was found to be more than the duration required for cross linking of activated polysaccharide to activated polysaccharide thereby resulting in formation of aggregates. Refer FIGS. 3 & 4.

However for other serotypes like 6APnPs and 6BPnPs, such cross linking was not observed.

Example 11

Preparation of Conjugates: PnPs19A & PnPs19F

Conjugation of polysaccharide to carrier protein was carried out using CDAP conjugation method of Lees et al (Vaccine 26: 190-198, 1996) with following modifications:

i) For preparing 19A conjugate, using a polysaccharide to CDAP ratio of 1:1 at 22° C. with a period of activation of 4 min and using a polysaccharide to protein ratio of 1:1 ii) For preparing 19F conjugate, using a polysaccharide to CDAP ratio of 1:0.8 at 22° C. with a period of activation of 9 to 10 min and a polysaccharide to protein ratio of 1:1 for 19F.

TABLE 10

Comparison of conjugate results for 19A and 19F with "traditional CDAP conjugation method" (Lot 1) and "improved conjugation method" (Lot 2)

| I) Conjugation Reaction details | | | | |
|---|---|---|---|---|
| Conjugates | 19A conjugate | | 19F conjugate | |
| Batch Number | Lot 1 | Lot 2 | Lot 1 | Lot 2 |
| PnPs Conc. (mg/ml) | 9.5 | 9.5 | 9.5 | 9.5 |
| PnPs dissolution | 2M NaCl | 2M NaCl | 2M NaCl | 2M NaCl |
| Activation time (min) | 4 | 4 | 4 | 9 to 10 |
| Ratio PnPs/CDAP | 1.0:1.5 | 1.0:1.0 | 1.0:1.5 | 1.0:0.8 |
| CRM Conc (mg/ml) | 20 | 20 | 20 | 20 |
| Initial Ratio Ps/CRM$_{197}$ | 1.0:1.5 | 1.0:1.0 | 1.0:1.5 | 1.0:1.0 |
| pH$^a$:pH$^c$:pH$^q$ | 9.0:9.0:9.0 | 9.0:9.0:9.0 | 9.5:9.5:9.5 | 9.5:9.5:9.5 |
| II) Final Conjugate Characteristics | | | | |
| Conjugates | 19A conjugate | | 19F conjugate | |
| Batch Number | Lot 1 | Lot 2 | Lot 1 | Lot 2 |
| Final Ratio PnPs/CRM$_{197}$ | 0.53 | 0.86 | 0.52 | 0.96 |
| CRM$_{197}$/PnPs | 1.88 | 1.16 | 1.92 | 1.04 |
| Free PnPs (%) | 1.9 | 1.5 | 1.7 | 1.07 |
| Free CRM$_{197}$ (%) | ND | ND | ND | 2.2 |
| Avg. Mol. Size SEC-HP-I)(KDa) | 1081 | 853 | 994 | 847 |
| Avg. Mol. size (UV/RI/MALS) (KDa) | 8212 | 6012 | 6393 | 4773 |

Results:

It was observed that modified Polysaccharide:CDAP ratio, CDAP activation time and initial polysaccharide: protein ratio, were found to minimize 4-dimethylaminopyridine mediated degradation of sized polysaccharide during activation and also prevented subsequent polysaccharide-polysaccharide aggregation thereby improving final conjugate characteristics with respect to free polysaccharide content.

The improved conjugation method employed for preparing 19 A & 19F conjugates resulted in conjugates that did not show any phosphomonoester signal in respective conjugate profiles ($^{31}$P Proton NMR) which indicated that modified conjugation method was found to be effective in preventing hydrolysis of polysaccharides across conjugation reactions.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A stable multivalent *Streptococcus pneumoniae* polysaccharide-protein conjugate vaccine composition comprising at least 10 distinct *Streptococcus pneumoniae* polysaccharide protein conjugates having polysaccharide selected from serotypes 1, 2, 3, 4, 5, 6A, 6B, 7F, 8, 9A, 9V, 9F, 9N, 10A, 11 A, 12F, 14, 15A, 15B, 15C, 17F, 18C, 19A, 19F, 20, 22F, 23B, 23F, 24F, 33F, 35B, 38 and 45, wherein at least one polysaccharide protein conjugate has CRM197 as a carrier protein, at least one polysaccharide protein conjugate has tetanus toxoid (TT) as carrier protein, and at least one polysaccharide protein conjugate has diphtheria toxoid (DT) as carrier protein, wherein serotypes 6A, 9V and 23 F are individually adsorbed on an aluminium adjuvant, serotypes selected from 1, 2, 3, 4, 5, 6B, 7F, 12F, 14, 15B, 18C, 19A, 19F, and 22F are mixed and adsorbed to an aluminum adjuvant, and the adsorption is in the range of 75-99%, and wherein said composition has histidine-succinic acid buffer in a concentration between 10 mM and 40 mM.

2. The composition according to claim 1; wherein said composition comprises of 10 distinct *Streptococcus pneumoniae* polysaccharide protein conjugates having polysaccharide from serotypes 1, 5, 6A, 6B, 7F, 9V, 14, 19A, 19F and 23F.

3. The composition according to claim 1; wherein said composition comprises of 16 distinct *Streptococcus pneumoniae* polysaccharide protein conjugates having polysaccharide from serotypes 1, 2, 3, 4, 5, 6A, 6B, 7F, 9V, 12F, 14, 15B, 18C, 19A, 19F, and 23F, wherein serotype 3 is conjugated to CRM197, serotype 18C is conjugated to CRM197, Serotype 4 is conjugated to DT, serotype 15B is conjugated to TT.

4. The composition according to claim 1, wherein serotype 3 is conjugated to CRM197, serotype 18C is conjugated to CRM197, Serotype 4 is conjugated to DT, serotype 15B is conjugated to TT and serotype 22F is conjugated to TT.

5. The composition of claim 1, existing in a lyophilized state, further comprising a diluent containing aluminium phosphate gel and NaCl.

6. The composition according to claim 1; wherein said composition comprises 17 distinct *Streptococcus pneumoniae* polysaccharide protein conjugates having polysaccharide from serotypes 1, 2, 3, 4, 5, 6A, 6B, 7F, 9V, 12F, 14, 15B, 18C, 19A, 19F, 22F and 23F, wherein serotype 3 is conjugated to CRM197, serotype 18C is conjugated to CRM197, Serotype 4 is conjugated to DT, serotype 15B is conjugated to TT and serotype 22F is conjugated to TT.

7. The composition of claim 1, wherein *Streptococcus pneumoniae* serotype 6A-CRM197 conjugate exhibits an increased immunogenicity when present in 16 valent or 17 valent composition.

8. A stable multivalent *Streptococcus pneumoniae* polysaccharide-protein conjugate vaccine composition comprising 10 distinct *Streptococcus pneumoniae* polysaccharide protein conjugates having polysaccharide from serotypes 1, 5, 6A, 6B, 7F, 9V, 14, 19A, 19F, and 23F wherein the polysaccharides are conjugated to CRM197 as the carrier protein, wherein serotype 6A, 9V and 23 F are individually adsorbed on an aluminium adjuvant, serotypes selected from 1, 5, 6B, 7F, 14, 19A, and 19F are mixed and adsorbed to an aluminum adjuvant, and the adsorption is in the range of 75-99%, and wherein said composition has histidine-succinic acid buffer in a concentration between 10 mM and 40 mM.

* * * * *